United States Patent
Bazan et al.

(12) 
(10) Patent No.: US 6,864,271 B2
(45) Date of Patent: Mar. 8, 2005

(54) SYNERGISTIC COMBINATIONS INCLUDING N-ACYLATED 4-HYDROXYPHENYLAMINE DERIVATIVES

(75) Inventors: Nicolas G. Bazan, New Orleans, LA (US); Dennis Paul, New Orleans, LA (US); Carlos Sunkel, Madrid (ES); Julio Alvarez-Builla, Madrid (ES)

(73) Assignee: The Foundation for the LSU Health Sciences Center, New Orleans, LA (US)

( * ) Notice: Subject to any disclaimer, the term of this patent is extended or adjusted under 35 U.S.C. 154(b) by 0 days.

(21) Appl. No.: 10/292,105

(22) Filed: Nov. 12, 2002

(65) Prior Publication Data

US 2004/0092541 A1 May 13, 2004

(51) Int. Cl.[7] .............................................. A61K 31/425
(52) U.S. Cl. ...................................................... 514/373
(58) Field of Search ......................................... 514/373

(56) References Cited

U.S. PATENT DOCUMENTS

| | | | |
|---|---|---|---|
| 4,599,342 A | | 7/1986 | LaHann |
| 4,812,446 A | | 3/1989 | Brand |
| 5,554,636 A | * | 9/1996 | Bazan et al. ................. 514/373 |
| 5,621,110 A | * | 4/1997 | Bazan et al. ................. 548/210 |
| 5,869,498 A | | 2/1999 | Mayer et al. |
| 6,048,540 A | | 4/2000 | Kim et al. |
| 6,143,278 A | * | 11/2000 | Elkhoury ...................... 424/45 |
| 6,538,008 B1 | * | 3/2003 | Boyce .......................... 514/317 |
| 6,632,217 B2 | * | 10/2003 | Harper et al. ............. 604/892.1 |

* cited by examiner

*Primary Examiner*—Sreeni Padmanabhan
*Assistant Examiner*—Jennifer Kim
(74) *Attorney, Agent, or Firm*—Adams and Reese LLP

(57) ABSTRACT

The present invention relates to pharmaceutical combinations of opioid and non-opioid analgesics in an intimate admixture with an analgesic from a series of N-acylated 4-hydroxyphenylamine derivatives, linked via an alkylene bridge to the nitrogen atom of a 1,2-benzisothiazol-3(2H)-one 1,1-dioxide group and methods for their use to alleviate pain in mammals. The analgesic combinations exhibit enhanced analgesic potency, do not suppress blood coagulation, and have little hepatotoxic effect.

48 Claims, 3 Drawing Sheets

SYNERGISTIC COMBINATIONS INCLUDING N-ACYLATED 4-HYDROXYPHENYLAMINE DERIVATIVES

CROSS REFERENCE TO RELATED APPLICATIONS

Not applicable

STATEMENT REGARDING FEDERALLY SPONSORED RESEARCH OR DEVELOPMENT

Not applicable

REFERENCE TO A MICROFICHE APPENDIX

Not applicable

COPYRIGHT NOTICE

Not applicable

FIELD OF THE INVENTION

The present invention relates to analgesic compositions for enhancing the efficacy and/or potency of certain opioid and non-opioid analgesics that do not suppress blood coagulation, and have little hepatotoxic effect. More particularly, the present invention relates to analgesic compositions that include analgesics referred to as the SCP series (SCP-1 through SCP-5) in combination with opioid and non-opioid analgesics.

BACKGROUND OF THE INVENTION

Drug combinations such as acetaminophen with codeine (Tylenol III) or acetaminophen with oxycodone (Lortab) produce analgesia that is additive or synergistic. The rational for using such combinations is to reduce the dose of each analgesic, and thus reduce adverse effects and toxicity, while retaining or increasing analgesic efficacy. These acetaminophen combinations have greater efficacy for moderate to severe pain.

For many types of pain (e.g., common headache, osteoarthritis) acetaminophen has equal potency and efficacy to acetylsalicylic acid (aspirin). However, the safety of acetaminophen has been questioned. There are approximately 100,000 cases of acetaminophen overdose annually, with approximately 30 deaths resulting. (Clissold, 1980; McGoldrick et al. 1997). Acetaminophen has a toxic metabolite, N-acetyl-benzoquinoneimine (NAPQI), which depletes hepatic and renal glutathione, a cytoprotective endogenous metabolite (Mason & Fischer, 1986; Mitchell et al., 1983). Hepatic and renal toxicity with acetaminophen can occur at doses only 4- to 8-fold higher than the maximum recommended analgesic dose (Neuberger et al., 1980). Pharmaceutical combinations that contain acetaminophen and a centrally acting analgesic may be even more dangerous than acetaminophen alone. With repeated use these combinations require higher doses to produce the same analgesic effect because of an increase in tolerance. As the dose of the combination is increased to compensate for analgesic tolerance, the safety of the drug decreases as the higher doses of the acetaminophen component increase hepatic and renal toxicity.

In U.S. Pat. No. 5,554,636 (Bazan et al.) and U.S. Pat. No. 5,621,110 (Bazan et al.), two of the inventors herein disclosed the series of N-acylated 4-hydroxyphenylamine derivatives linked via an alkylene bridge to the nitrogen atom of a 1,2-benzisothiazol-3(2H)-one 1,1-dioxide group along with the process for their preparation and methods of their use for alleviating pain. The disclosures of these patents are incorporated herein by reference. The SCP series is structurally depicted by the following general formula:

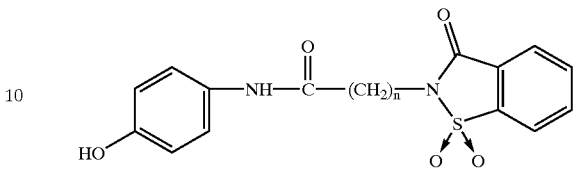

wherein n is a number from 1 to 5. These new non-narcotic analgesics surprisingly possess high analgesic activity, do not suppress blood coagulation, and display little hepatotoxic effect. When the term "SCP series" is used herein, it is understood that any of the pharmaceutically suitable salts thereof are included by the term.

The analgesic profiles of the SCP series are at least as good as that of acetaminophen. As expected, both types of drugs show little or no activity in the tail-flick and hotplate tests when compared with codeine. SCP-1 is more potent in the abdominal stretch, formalin, and Freund's adjuvant-induced inflammation assays of analgesia than acetaminophen. SCP-1 is lower in toxicity, and, of even greater importance, lower in hepatotoxicity (Paul et al., 1998). All of these properties make SCP-1 and related derivatives potentially very useful pharmacologic agents.

OBJECTS AND SUMMARY OF THE INVENTION

It is an object of the invention to provide pharmaceutical combinations comprising an analgesic from the SCP series along with an opioid or a non-opioid analgesic that has an analgesic profile at least as good as acetaminophen/opioid analgesic or acetaminophen/non-opioid analgesic combinations.

It is another object of the invention to provide pharmaceutical combinations comprising an analgesic from the SCP series along with an opioid or non-opioid analgesic that has lower hepatotoxicity than acetaminophen/opioid analgesic or acetaminophen/non-opioid analgesic combinations.

It is still another object of the invention to provide pharmaceutical combinations comprising an analgesic from the SCP series along with an opioid or non-opioid analgesic that does not suppress blood coagulation, and therefore can be used as a pre-emptive analgesic for procedures expected to produce post-surgical pain.

DESCRIPTION OF THE PREFERRED EMBODIMENTS

Figure 1:
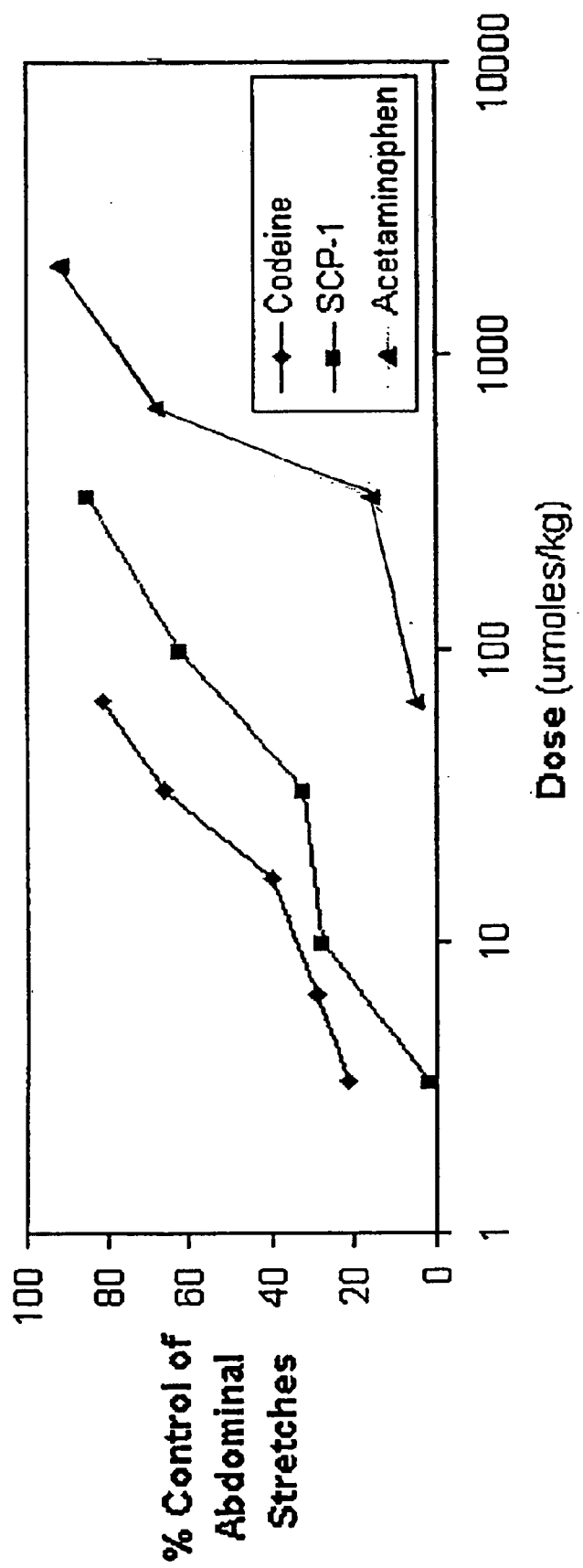
FIG. 1 shows the analgesic effect of SCP-1 compared to codeine and acetaminophen.

The most commonly employed method of managing pain involves the systemic administration of analgesics. Analgesics by definition include drugs that through their action on the nervous system reduce or abolish the perception of pain without producing unconsciousness. Traditionally, analgesics fall into two broad categories: (1) simple, non-narcotic analgesics, such as aspirin, which appear to work by inhibition of prostaglandin synthetase, and (2) narcotic analgesics, which appear to work through interaction with the endorphin/enkephalin receptor system of the central nervous system. The term "narcotic" has historically been associated with the strong opioid analgesics, but the term is not very useful in a pharmacological context. More appropriately, the category referred to as narcotic analgesics, can be further divided into two groups, the opioids and non-opioids. The term "opioids" refers to drugs with morphine like activity (agonists and antagonists), acting on mu, delta and kappa receptors. The term "non-opioids" refers to drugs that act via a different mechanism.

The drugs that comprise the group known as the opioid analgesics include among others the phenanthrene alkaloids of opium, comprising morphine, codeine, and thebaine. While thebaine produces no analgesia, it is an important intermediate in the production of semisynthetic opioids. Other agents with structures and function related to morphine include: (1) the morphine analogs, such as hydromorphone, oxymorphone, hydrocodone, and oxycodone; (2) Diels-Alder adducts, such as etorphine and buprenorphine; (3) the morphinan derivatives, such as dextromethorphan and butorphanol; (4) the benzomorphan derivatives, such as phenazocine, pentazocine and cyclazocine; (5) the piperidine derivatives, such as meperidine and anileridine; and (6) open chain analgesics (methadone type compounds), such as methadone and propoxyphene. The drugs that comprise the group known as the non-opioid analgesics include: (1) N-methyl-D-aspartate (NMDA) receptor antagonists, such as dextromethorphan and ketamine and other antagonists that suppress central sensitization by competing for any of the binding site subcategories associated with the NMDA receptor, e.g., the glycine binding site, the phenylcyclidine (PCP) binding site, etc., as well as the NMDA channel; (2) alpha$_2$ adrenoreceptor agonists, such as clonidine, metomidine, detomidine, dexmetomidine, dexmedetomidine and xylazine, that reduce the release of norepinephrine; (3) other agents, such as tramadol, often mistakenly referred to as an opioid, that produce analgesia by their inhibitory actions on monoamine re-uptake rather than by agonist effect; (4) non-steroidal anti-inflammatory drugs such as aspirin, ibuprofen and other drugs that inhibit cyclooxygenase enzymes and (5) mixed agonist-antagonist analgesics such as buprenorphine, dezocine, nalbuphine.

Opioid and non-opioid analgesics may cause a variety of side effects including sedation, constipation, hypotension, nausea, vomiting, elevation of cerebrospinal fluid pressure, respiratory depression, physical dependence and tolerance. Therefore, there is a serious need to develop combinations of drugs that supplement the activity of the opioid and non-opioid analgesics, which allows the use of smaller doses of the opioid and non-opioid analgesics. One way of achieving this result is to enhance the analgesic activity of a known opioid or non-opioid analgesic by the addition of a second non-narcotic analgesic. However, it is difficult to predict when a synergistic effect will be obtained from two pharmaceutical compositions that take effect through different mechanisms.

The SCP series are non-narcotic analgesics that have little hepatotoxic effect. The compounds in this series do not produce the metabolite that is responsible for acetaminophen toxicity. As a result, they are more useful than acetaminophen and other non-narcotic analgesics in the treatment of chronic pain. Moreover, unlike conventional non-narcotic analgesics, such as aspirin or ibuprofen, the SCP series does not suppress blood coagulation. Children, the elderly and liver-compromised patients would also benefit from the administration of SCP for the treatment of pain. Pharmaceutical combinations utilizing the SCP series with opioid and non-opioid analgesics has been found to provide enhanced analgesia, without suppressing blood coagulation, and without the toxicity associated with conventional non-narcotic analgesics.

The pharmaceutical combinations of the present invention comprise an opioid or a non-opioid analgesic in an intimate admixture with an analgesic from the SCP series along with a pharmaceutically acceptable carrier prepared according to conventional pharmaceutical techniques. Pharmaceutically acceptable carriers include solid or liquid fillers, diluents, and encapsulating substances. The amount of the carrier employed in conjunction with the combination is sufficient to provide a practical quantity of material per unit dose of analgesic.

Pharmaceutically acceptable carriers for oral administration include, sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Pharmaceutically acceptable carriers for parenteral administration include isotonic saline, propylene glycol, ethyl oleate, pyrrolidone, aqueous ethanol, sesame oil, corn oil, and combinations thereof.

Various oral dosages forms can be employed, including solid forms such as tablets, capsules, granules and bulk powders. Tablets can be compressed, tablet triturates, enteric-coated, sugar-coated, film-coated or multiple compressed, containing suitable binders, lubricants, diluents, disintegrating agents, coloring agents, flavoring agents, flow-inducing agents, and melting agents. Liquid oral dosage forms include aqueous solutions, emulsions, suspensions, and reconstituted solutions and/or suspensions.

Pharmaceutically effective combinations can contain between 0.1 and 1000 mg of an analgesic from the SCP series. The preferred pharmaceutically effective combinations contain between 400 and 1000 mg of an analgesic from the SCP series. The pharmaceutically effective amounts of the opioid and non-opioid analgesics in combination with analgesics in the SCP series are similar to the corresponding combinations of opioid and non-opioid analgesics with acetaminophen. The following examples are illustrative of pharmaceutically effective combinations of the present invention:

| Example 1: Codiene | |
|---|---|
| Dosage of SCP (mg): | 100–1000 |
| Dosage of Codiene (mg): | 0.1–100 |
| Preferred Ratios for Oral Dosage (mg codeine:mg SCP): | 15:450 |
| | 30:450 |
| | 60:450 |
| Preferred Weight Ratios for Injectable Delivery (codeine:SCP): | 1:10 |
| | 1:5 |
| Example 2: Morphine | |
| Dosage of SCP (mg): | 100–1000 |
| Dosage of Morphine (mg): | 0.1–100 |
| Preferred Ratios for Oral Dosage (mg morphine:mg SCP): | 15:450 |
| | 30:450 |
| | 60:450 |

-continued

| | |
|---|---|
| Preferred Weight Ratios for Injectable Delivery (morphine:SCP): | 1:60 |
| | 1:30 |
| Example 3: Hydrocodone | |
| Dosage of SCP (mg): | 100–1000 |
| Dosage of Hydrocodone (mg): | 0.1–100 |
| Preferred Ratios for Oral Dosage (mg hydrocodone:mg SCP): | 2.5:450 |
| | 5:450 |
| | 7.5:450 |
| | 10:450 |
| Preferred Weight Ratios for Injectable Delivery (hydrocodone:SCP): | 1:200 |
| | 1:100 |
| Example 4: Dihydrocodone | |
| Dosage of SCP (mg): | 100–1000 |
| Dosage of Dihydrocodone (mg): | 0.1–100 |
| Preferred Ratios for Oral Dosage (mg dihydrocodone:mg SCP): | 10:450 |
| | 36:450 |
| Preferred Weight Ratios for Injectable Delivery (dihydrocodone:SCP): | 1:100 |
| | 1:50 |
| Example 5: Oxycodone | |
| Dosage of SCP (mg): | 100–1000 |
| Dosage of Oxycodone (mg): | 0.1–100 |
| Preferred Ratios for Oral Dosage (mg oxycodone:mg SCP): | 5:450 |
| Preferred Weight Ratios for Injectable Delivery (oxycodone:SCP): | 1:200 |
| Example 6: Controlled Release Oxycodone | |
| Dosage of SCP (mg): | 100–1000 |
| Dosage of Oxycodone (mg): | 0.1–100 |
| Preferred Weight Ratios for Oral Dosage (mg oxycodone:mg SCP): | 10:900 |
| | 20:900 |
| | 40:900 |
| | 60:900 |
| Example 7: Meperidine | |
| Dosage of SCP (mg): | 100–1000 |
| Dosage of Meperidine (mg): | 0.1–500 |
| Preferred Ratios for Oral Dosage (mg merperidine:mg SCP): | 25:450 |
| | 50:450 |
| Preferred Weight Ratios for Injectable Delivery (merperidine:SCP): | 1:20 |
| | 1:10 |
| Example 8: Propoxyphene | |
| Dosage of SCP (mg): | 100–1000 |
| Dosage of Propoxyphene (mg): | 0.1–500 |
| Preferred Ratios for Oral Dosage (mg propoxyphene:mg SCP): | 65:450 |
| | 100:450 |
| Preferred Weight Ratios for Injectable Delivery (propoxyphene:SCP): | 1:10 |
| Example 9: Levorphanol | |
| Dosage of SCP (mg): | 100–1000 |
| Dosage of Levorphanol (mg): | 0.1–100 |
| Preferred Ratios for Oral Dosage (mg levorphanol:mg SCP): | 4:450 |
| Preferred Weight Ratios for Injectable Delivery (levorphanol:SCP): | 1:100 |
| Example 10: Oxymorphone | |
| Dosage of SCP (mg): | 100–1000 |
| Dosage of Oxymorphone (mg): | 0.1–200 |
| Preferred Ratios for Oral Dosage (mg oxymorphone:mg SCP): | 5:450 |
| Preferred Weight Ratios for Injectable Delivery (oxymorphone:SCP): | 1:100 |
| Example 11: Hydromorphone | |
| Dosage of SCP (mg): | 100–1000 |
| Dosage of Hydromorphone (mg): | 0.1–100 |
| Preferred Ratios for Oral Dosage (mg hydromorphone:mg SCP): | 1:450 |
| | 3:450 |
| | 5:450 |
| | 8:450 |
| Preferred Weight Ratios for Injectable Delivery (hydromorphone:SCP): | 1:450 |
| | 1:150 |
| | 1:100 |

-continued

| | |
|---|---|
| | 1:50 |
| Example 12: Fentanyl | |
| Dosage of SCP (mg): | 100–1000 |
| Dosage of Fentanyl (mcg): | 0.1–500 |
| Preferred Ratios for Oral Dosage (mcg fentanyl:mg SCP): | 10:450 |
| | 50:450 |
| Preferred Weight Ratios for Injectable Delivery (fentanyl:SCP): | 1:1000 |
| Example 13: Alfentanyl | |
| Dosage of SCP (mg): | 100–1000 |
| Dosage of Alfentanyl (mcg): | 0.01–50 |
| Preferred Ratios for Oral Dosage (mcg alfentanyl:mg SCP): | 1:450 |
| | 5:450 |
| Preferred Weight Ratios for Injectable Delivery (alfentanyl:SCP): | 1:10000 |
| Example 14: Sufentanyl | |
| Dosage of SCP (mg): | 100–1000 |
| Dosage of Sufentanyl (mcg): | 0.1–500 |
| Preferred Ratios for Oral Dosage (mcg sufentanyl:mg SCP): | 10:450 |
| | 50:450 |
| Preferred Weight Ratios for Injectable Delivery (sufentanyl:SCP): | 1:10000 |
| Example 15: Remifentanyl | |
| Dosage of SCP (mg): | 100–1000 |
| Dosage of Remifentanyl (mcg): | 0.1–500 |
| Preferred Ratios for Oral Dosage (mcg remifentanyl:mg SCP): | 1:450 |
| | 5:450 |
| Preferred Weight Ratios for Injectable Delivery (remifentanyl:SCP): | 1:100000 |
| Example 16: Levomethadyl | |
| Dosage of SCP (mg): | 100–1000 |
| Dosage of Levomethadyl (mg): | 0.1–200 |
| Preferred Ratios for Oral Dosage (mg levomethadyl:mg SCP): | 10:450 |
| | 140:450 |
| Preferred Weight Ratios for Injectable Delivery (levomethadyl:SCP): | 1:10 |
| | 1:4 |
| Example 17: Methadone | |
| Dosage of SCP (mg): | 100–1000 |
| Dosage of Methadone (mg): | 0.1–200 |
| Preferred Ratios for Oral Dosage (mg methadone:mg SCP): | 5:450 |
| | 10:450 |
| | 40:450 |
| Preferred Weight Ratios for Injectable Delivery (methadone:SCP): | 1:100 |
| | 1:50 |
| | 1:10 |
| Example 18: Buprenorphine | |
| Dosage of SCP (mg): | 100–1000 |
| Dosage of Buprenorphine (mg): | 0.01–100 |
| Preferred Ratios for Oral Dosage (mg buprenorphine:mg SCP): | 1:450 |
| Preferred Weight Ratios for Injectable Delivery (buprenorphine:SCP): | 1:100 |
| Example 19: Butorphanol | |
| Dosage of SCP (mg): | 100–1000 |
| Dosage of Butorphanol (mg): | 0.1–200 |
| Preferred Ratios for Oral Dosage (mg butorphanol:mg SCP): | 20:450 |
| Preferred Weight Ratios for Injectable Delivery (butorphanol:SCP): | 1:20 |
| Example 20: Dezocine | |
| Dosage of SCP (mg): | 100–1000 |
| Dosage of Dezocine (mg): | 0.1–200 |
| Preferred Ratios for Oral Dosage (mg dezocine:mg SCP): | 15:450 |
| | 30:450 |
| | 60:450 |
| Preferred Weight Ratios for Injectable Delivery (dezocine:SCP): | 1:60 |
| | 1:30 |

-continued

Example 21: Nalbuphine

| | |
|---|---|
| Dosage of SCP (mg): | 100–1000 |
| Dosage of Nalbuphine (mg): | 0.1–200 |
| Preferred Ratios for Oral Dosage (mg nalbuphine:mg SCP): | 50:450 |
| Preferred Weight Ratios for Injectable Delivery (nalbuphine:SCP): | 1:60 |

Example 22: Pentazocine

| | |
|---|---|
| Dosage of SCP (mg): | 100–1000 |
| Dosage of Pentazocine (mg): | 0.1–500 |
| Preferred Ratios for Oral Dosage (mg pentazocine:mg SCP): | 25:450 50:450 |
| Preferred Weight Ratios for Injectable Delivery (pentazocine:SCP): | 1:20 1:10 |

Example 23: Tramadol

| | |
|---|---|
| Dosage of SCP (mg): | 100–1000 |
| Dosage of Tramadol (mg): | 0.1–500 |
| Preferred Ratios for Oral Dosage (mg tramadol:mg SCP): | 50:450 |
| Preferred Weight Ratios for Injectable Delivery (tramadol:SCP): | 1:10 |

Example 24: Clonidine

| | |
|---|---|
| Dosage of SCP (mg): | 100–1000 |
| Dosage of Clonidine (mg): | 0.01–100 |
| Preferred Ratios for Oral Dosage (mg clonidine:mg SCP): | 1:450 |
| Preferred Weight Ratios for Injectable Delivery (clonidine:SCP): | 1:450 |

Example 25: Aspirin

| | |
|---|---|
| Dosage of SCP (mg): | 100–1000 |
| Dosage of Aspirin (mg): | 0.1–1000 |
| Preferred Ratios for Oral Dosage (mg aspirin:mg SCP): | 250:450 |
| Preferred Weight Ratios for Injectable Delivery (aspirin:SCP): | 1:2 |

As shown in FIG. 1, the analgesic potency of SCP-1 is greater than that of acetaminophen in the abdominal stretch assay. In this assay of pain, the number of stretches exhibited by a mouse after an intraperitoneal (i.p.) injection of dilute acetic acid (Koster et al., 1959) are counted. The analgesic compounds (acetaminophen, SCP-1, or codeine) were administered orally and fifty-five minutes later, the mice (groups of 8 or more) received an i.p. injection of 10 ml/kg of 0.4% acetic acid. The number of abdominal stretches was counted beginning 5 minutes after the acetic acid injection for a period of 10 minutes. For each of the compounds tested, the percentage of the number of stretches obtained in control animals (29±2.1) was calculated. All three compounds produced a dose-dependent decrease in the number of abdominal stretches, however, the potency of SCP-1 was significantly greater than acetaminophen.

Figure 2:
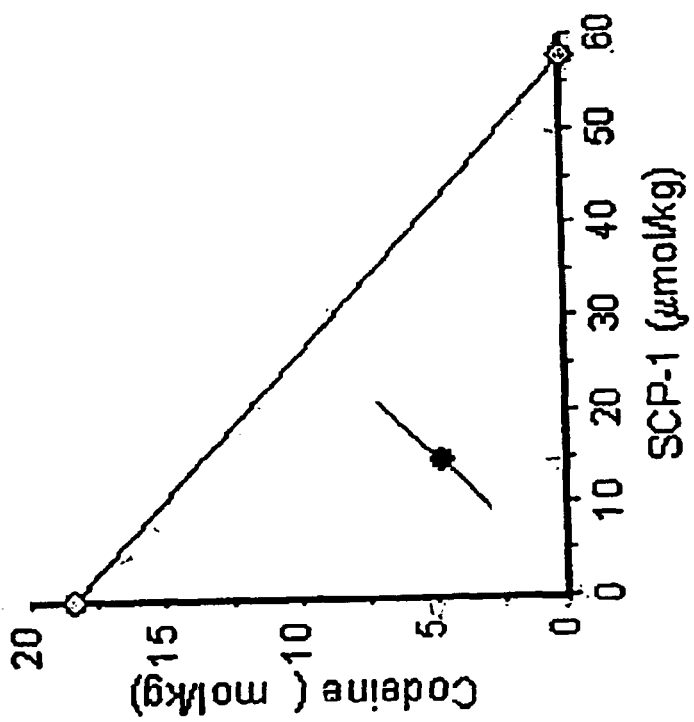
FIG. 2 shows an isobologram for acetaminophen and codeine compared to an isobologram for SCP-1 and codeine.
Figure 2:
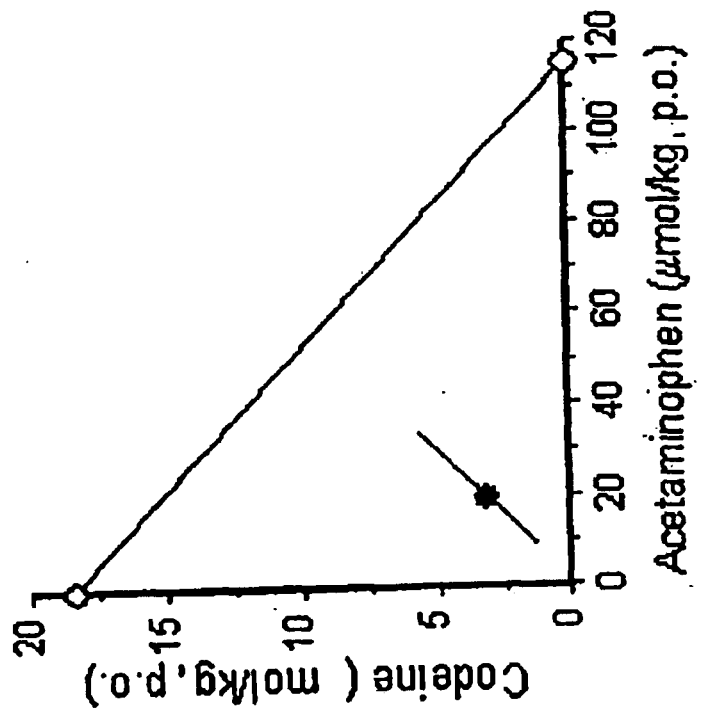

As shown in FIG. 2, an isobolographic analysis was performed to demonstrate the synergistic effect of an SCP-1/narcotic analgesic pharmaceutical combination. The isobologram is a quantitative method for measuring interactions between drugs where dose-effect relationships are depicted in a multi-dimensional array with lines connecting dose pairs that are equieffective in relationship to a common pharmacological endpoint. Most importantly, the isobolographic analysis permits a full range of doses and dose combinations to be examined where the proportion of the first drug to the second actually varies from 0 to infinity, and to determine, by virtue of the graphical display, whether any one or more of the paired drug combinations displays unique pharmacological properties in comparison to the entire body of generated data.

Groups of mice (n=10) were administered a dose of acetaminophen, SCP-1, or codeine to define a dose-response curve for each drug in the abdominal stretch assay. The $ED_{50}$ for each drug was calculated using nonlinear regression analysis. Subsequently, a combination of acetaminophen and codeine or a combination of SCP-1 and codeine was tested using the same assay. The ratios of acetaminophen to codeine or SCP-1 to codeine were equivalent to the ratios of the $ED_{50}$s of each drug alone. Dose-response curves for the drug combination ratios were produced and $ED_{50}$s calculated. The $ED_{50}$s were graphed according to the method of Tallarida et al., (1997). Briefly, the dose of one drug is depicted on the X-axis with a linear scale and a range of 0 to its $ED_{50}$. The dose of the other drug is likewise depicted on the Y-axis. A line is drawn diagonally from $ED_{50}$ to $ED_{50}$. This line is known as the line of additivity, as any combination of X and Y doses that fall upon this line would be predicted to produce 50% analgesia. The experimental $ED_{50}$ is plotted according to the dose of each individual drug and the standard error oriented on a line from the origin through the data point. Thus, when the $ED_{50}$ of the drug combination is plotted, any point (± standard error) closer to the origin than the line of additivity would be considered to be synergistic (producing more analgesia than expected based on simple additivity) and any point farther from the origin than the line of additivity would be considered to be antagonistic (producing less analgesia than expected based on simple additivity). The combination of acetaminophen and codeine produced analgesia synergistically (see FIG. 2A). The combination of SCP-1 and codeine also produced analgesia synergistically (see FIG. 2B).

Figure 3:
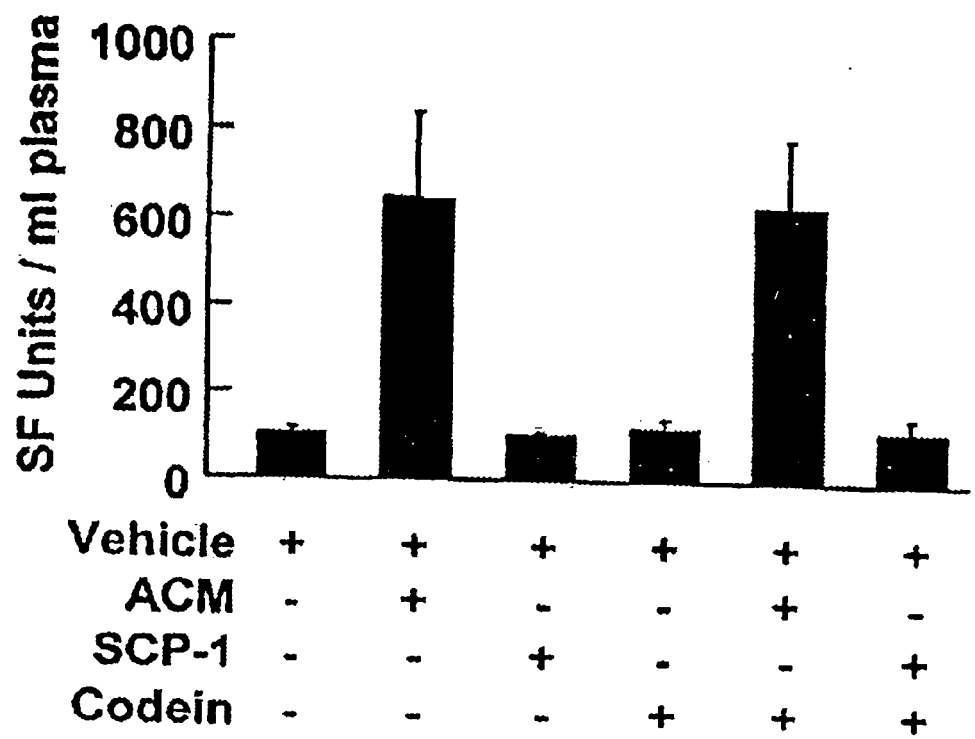
FIG. 3 shows the hepatotoxicity of SCP-1 alone and in combination with codeine compared to acetaminophen alone and in combination with codeine in C57/b16 mice.

A study was also devised to assess the toxicity of SCP-1 in combination with codeine in comparison to the toxicity of acetaminophen in combination with codeine, the results of which are depicted in FIG. 3. The study was performed on C57/b16 mice weighing 22–25 g. The mice were administered doses of acetaminophen, SCP-1, codeine, a combination of acetaminophen and codeine, or a combination of SCP-1 and codeine in a corn oil vehicle using an esophageal cannula. The administered doses of acetaminophen and SCP-1 were equivalent to the acetaminophen LD50 in mice (3.7 mmole/kg) and the administered dose of codeine was 50 mg/kg. After 24 hours, plasma activity levels of glutamic/pyruvic transaminase (GPT) and glutamic/oxalacetic transarninase (GOT) were obtained to assess hepatotoxic levels of drugs. As shown in FIG. 3, acetaminophen produced a large increase in GPT activity in serum, but neither SCP-1 nor codeine, nor the combination of both, produced any significant increase in activities.

It is apparent from the instant specification that various modifications and changes may be made by those skilled in the art. It is therefore intended that the following claims be interpreted as covering all modifications and changes that fall within the true spirit and scope of the invention.

What is claimed is:

1. An analgesic composition comprising pharmaceutically effective synergistic amounts of:

(a) an opioid analgesic;

(b) a non-narcotic analgesic of the general formula,

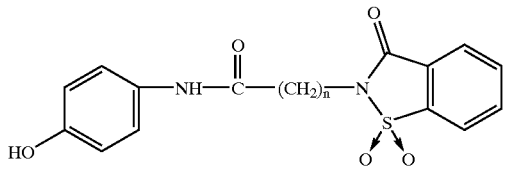

wherein n is a number from 1 to 5; and (c) a pharmaceuticaly acceptable carrier.

2. A composition according to claim 1, wherein the opioid analgesic is a phenanthrene alkaloid of opium.

3. A composition according to claim 1, wherein the opioid analgesic is selected from the group consisting of morphine and codeine.

4. A composition according to claim 1, wherein the opioid analgesic is a morphine analog.

5. A composition according to claim 1, wherein the opioid analgesic is selected from the group consisting of hydrocodone, oxycodone, hydromorphone, oxymorphone, metopon, apomorphine, normorphine, and N-(2-phenylethyl)-normorphine.

6. A composition according to claim 1, wherein the opioid analgesic is a synthetic derivative of thebaine.

7. A composition according to claim 1, wherein the opioid analgesic is selected from the group consisting of etorphine and buprenorphine.

8. A composition according to claim 1, wherein the opioid analgesic is a morphinan derivative.

9. A composition according to claim 1, wherein the opioid analgesic is selected from the group consisting of dextromethorphan, butorphanol, levorphanol, levallorphan, cyclorphan, and racemorphan.

10. A composition according to claim 1, wherein the opioid analgesic is a benzomorphan derivative.

11. A composition according to claim 1, wherein the opioid analgesic is selected from the group consisting of phenazocine, pentazocine, and cylcazocine.

12. A composition according to claim 1, wherein the opioid analgesic is a piperidine derivative.

13. A composition according to claim 1, wherein the opioid analgesic is selected from the group consisting of meperidine, anileridine, piminodine, ethoheptazine, alphaprodine, betaprodine, diphenoxylate, loperamide, fentanil, sufentanil, alfentanil, and remifentanil.

14. A composition according to claim 1, wherein the opioid analgesic is an open chain opioid analgesic.

15. A composition according to claim 1, wherein the opioid analgesic is selected from the group consisting of methadone, isomethadone, and propoxyphene.

16. An analgesic composition comprising pharmaceutically effective synergistic amounts of:

(a) a non-opioid analgesic;

(b) a non-narcotic analgesic of the general formula,

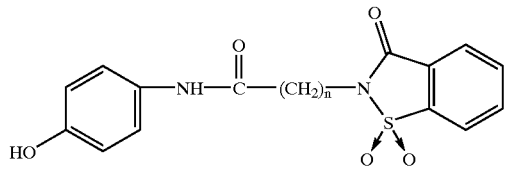

wherein n is a number from 1 to 5; and (c) a pharmaceutically acceptable carrier.

17. A composition according to claim 16, wherein the non-opioid analgesic is an NMDA receptor antagonist.

18. A composition according to claim 16, wherein the non-opioid analgesic is selected from the group consisting of dextromethorphan and ketamine.

19. A composition according to claim 16, wherein the non-opioid analgesic is an $alpha_2$ adrenoreceptor agonist.

20. A composition according to claim 16, wherein the non-opioid analgesic is selected from the group consisting of clonidine, metomidine, detomidine, dexmetomidine, dexmedetomidine and xylazine.

21. A composition according to claim 16, wherein the non-opioid analgesic is a monoamine re-uptake inhibitor.

22. A composition according to claim 16, wherein the non-opioid analgesic is tramadol.

23. A composition according to claim 16, wherein the non-opioid analgesic is a mixed agonist-antagonist analgesic.

24. A composition according to claim 16, wherein the non-opioid analgesic is selected from the group consisting of buprenorphine, dezocine and nalbuphine.

25. A method of alleviating pain in a mammal which comprises administering to said mammal affected with pain an effective amount of the composition of claim 1.

26. A method of alleviating pain in a mammal which comprises administering to said mammal affected with pain an effective amount of the composition of claim 2.

27. A method of alleviating pain in a mammal which comprises administering to said mammal affected with pain an effective amount of the composition of claim 3.

28. A method of alleviating pain in a mammal which comprises administering to said mammal affected with pain an effective amount of the composition of claim 4.

29. A method of alleviating pain in a mammal which comprises administering to said mammal affected with pain an effective amount of the composition of claim 5.

30. A method of alleviating pain in a mammal which comprises administering to said mammal affected with pain an effective amount of the composition of claim 6.

31. A method of alleviating pain in a mammal which comprises administering to said mammal affected with pain an effective amount of the composition of claim 7.

32. A method of alleviating pain in a mammal which comprises administering to said mammal affected with pain an effective amount of the composition of claim 8.

33. A method of alleviating pain in a mammal which comprises administering to said mammal affected with pain an effective amount of the composition of claim 9.

34. A method of alleviating pain in a mammal which comprises administering to said mammal affected with pain an effective amount of the composition of claim 10.

35. A method of alleviating pain in a mammal which comprises administering to said mammal affected with pain an effective amount of the composition of claim 11.

36. A method of alleviating pain in a mammal which comprises administering to said mammal affected with pain an effective amount of the composition of claim 12.

37. A method of alleviating pain in a mammal which comprises administering to said mammal affected with pain an effective amount of the composition of claim 13.

38. A method of alleviating pain in a mammal which comprises administering to said mammal affected with pain an effective amount of the composition of claim 14.

39. A method of alleviating pain in a mammal which comprises administering to said mammal affected with pain an effective amount of the composition of claim 15.

40. A method of alleviating pain in a mammal which comprises administering to said mammal affected with pain an effective amount of the composition of claim 16.

41. A method of alleviating pain in a mammal which comprises administering to said mammal affected with pain an effective amount of the composition of claim 17.

42. A method of alleviating pain in a mammal which comprises administering to said mammal affected with pain an effective amount of the composition of claim 18.

43. A method of alleviating pain in a mammal which comprises administering to said mammal affected with pain an effective amount of the composition of claim 19.

44. A method of alleviating pain in a mammal which comprises administering to said mammal affected with pain an effective amount of the composition of claim 20.

45. A method of alleviating pain in a mammal which comprises administering to said mammal affected with pain an effective amount of the composition of claim 21.

46. A method of alleviating pain in a mammal which comprises administering to said mammal affected with pain an effective amount of the composition of claim 22.

47. A method of alleviating pain in a mammal which comprises administering to said mammal affected with pain an effective amount of the composition of claim 23.

48. A method of alleviating pain in a mammal which comprises administering to said mammal affected with pain an effective amount of the composition of claim 24.

* * * * *

UNITED STATES PATENT AND TRADEMARK OFFICE
CERTIFICATE OF CORRECTION

| | | |
|---|---|---|
| PATENT NO. | : 6,864,271 B2 | Page 1 of 1 |
| APPLICATION NO. | : 10/292105 | |
| DATED | : March 8, 2005 | |
| INVENTOR(S) | : Nicolas G. Bazan et al. | |

It is certified that error appears in the above-identified patent and that said Letters Patent is hereby corrected as shown below:

In the Specification

At Column 1, Line number 13, change:
"Not applicable"

To:
--This invention was made with government support under EPS0092001 awarded by the National Science Foundation. The government has certain rights in the invention.--

Signed and Sealed this
Eighteenth Day of November, 2025

John A. Squires
*Director of the United States Patent and Trademark Office*